(12) United States Patent  
Loosen et al.

(10) Patent No.: US 7,058,618 B2  
(45) Date of Patent: Jun. 6, 2006

(54) METHOD FOR ESTABLISHING STRESS/STRAIN CURVES BY MEANS OF SPLINE INTERPOLATION ON THE BASIS OF CHARACTERISTIC POINTS AND WITH THE USE OF NEURAL NETWORKS

(75) Inventors: Roland Loosen, Erftstadt (DE); Thomas Mrziglod, Bergisch Gladbach (DE); Martin Wanders, Odenthal (DE); Klaus Salewski, Krefeld (DE); Bahman Sarabi, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 703 days.

(21) Appl. No.: 10/107,762

(22) Filed: Mar. 27, 2002

(65) Prior Publication Data

US 2002/0152426 A1 Oct. 17, 2002

(30) Foreign Application Priority Data

Apr. 4, 2001 (DE) .................................. 101 16 773

(51) Int. Cl.  
*G06N 3/02* (2006.01)

(52) U.S. Cl. ....................... 706/16; 706/20; 706/25

(58) Field of Classification Search .................. 706/16  
See application file for complete search history.

(56) References Cited

U.S. PATENT DOCUMENTS 6,430,993 B1* 8/2002 Seta .............................. 73/146

6,485,872 B1* 11/2002 Rosenthal et al. ............ 430/30

FOREIGN PATENT DOCUMENTS

DE 198 41 820 3/2000

OTHER PUBLICATIONS

Okuda, H. et al, Model of inelastic response using neural networks, May 1996, Transaction of the Japan Society of Mechanical Engineers, Part A v 62 n 597 p. 1284-1290.*

N. Huber et al, A neural network tool for identifying the material parameters of a finite deformation viscoplasitcity model with static recovery, Jan. 2001, Computer Methods in Applied Mechanics and Engineering, 191 (2001) 353-384.*

Ghabousi J et al: "Knowledge-based modeling of material behavior with neural networks" Journal of Engineering Mechanics, Bd. 117, Nr. 1, (Jan. 1991), Seiten 132-153, XP001088946 das ganze Dokument.

(Continued)

*Primary Examiner*—Anthony Knight  
*Assistant Examiner*—Ronald Williams  
(74) *Attorney, Agent, or Firm*—Joseph C. Gil; Aron Preis

(57) ABSTRACT

A stress/strain curve is established by means of neural networks 1 to N and 4. To that end, parameters are input into the input 50, from which the neural networks 1 to N respectively establish the principal components of characteristic points. The curve type is selected on the basis of the output of the neural network 4. The principal components of the characteristic points of the corresponding curve type are then inverse-transformed. The stress/strain curve is then calculated by the generator 59 on the basis of the inverse transformation.

16 Claims, 7 Drawing Sheets

OTHER PUBLICATIONS

Figure 1:
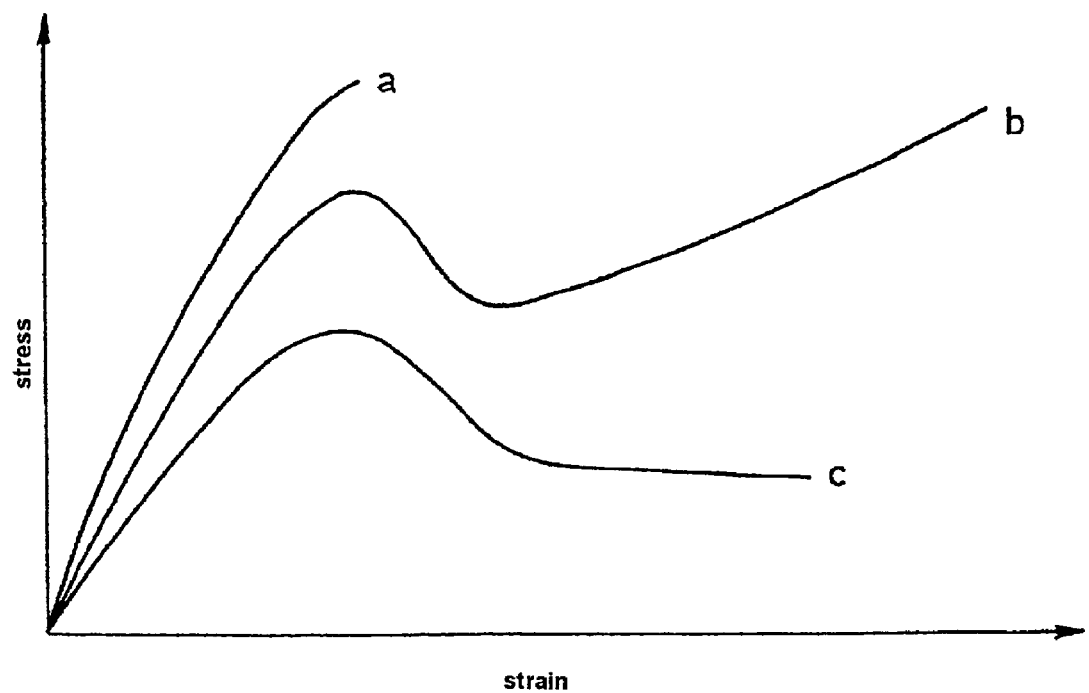

Wu X et al: "Representation of material behavior: neural network-based models" International Joint Conference on Neural Networks (IJCNN). San Diego, Jun. 17-21, New York, IEEE, US, Bd. 1, (Jun. 17, 1990), Seiten 229-234, XP000144219 Seite 230, Zeile 3—Seite 232, Absatz 1; Abbildungen 1-7.

Pernot S et al: "Application of neural networks to the modelling of some constitutive laws" Neural Networks, Elsevier Science Publishers, Barking, GB, Bd. 12, Nr. 2, Mar. 1999, Seiten 371-392, XP004157571 ISSN:0893-6080 Seite 380, Spalte 1, Zeile 1—Seite 391, Spalte 2, letzter Absatz; Abbildungen 14-25, 29 Seite 386, Spalte 2, Zeile 1—Seite 391, Spalte 2, Absatz 1; Abbildung 29.

Milligan R Vincent: "Computer Analysis of Mechanical Test Data Using Cubic Splines" ISA TRANS 1978, Bd. 17, Nr. 2, 1978, Seiten 21-30, XP001119082 Seite 22, Absatz 2—Seite 28, Absatz 1; Abbildungen 1, 6-11, 16-18.

Chen Hyland Y L Et Al: "Nonlinear Viscoelesticity of Hard Elastic Polypropylene Fibers" Spe Tech Conf, 33$^{rd}$ Annu, Proc; Atlanta, GA May 5-8, 1975, Seiten 265-267, XP001119088 1975 SPE, Greenwich, Conn Seite 266, Abschnitt "The Elastic Response in Simple Elongation" Abbildung 1.

Young Joel J: "Technique for determining yield point elongation" Symposium on automation of Mechanical Testing; Pittsburgh, PA, USA May 21, 1992, Nr. 1208, (May 21, 1992), Seiten 75-90, XP001119087 ASTM Spec Tech Publ; ASTM Special Technical Publication 1993 Publ by ASTM, Philadelphia, PA, USA Seite 80—Seite 89; Abbildungen 6, 7.

Mukherjee A et al: "Artificial neural networks in prediction of mechanical behavior of concrete at at high temperature" Nuclear Engineering And Design, Bd. 178, 1997, Seiten 1-11, XP002206975 Seite 4, Spale 2, Absatz 2—Seite 10, Spalte 2, Zeile 6; Abbildungen 1-8.

Millar D et al: "Investigation of back-propagation artificial neural networks in modelling the stress-strain behaviour of sandstone rock" Neural Networks, 1994, IEEE World Congress On Computation Intelligence, 1994 IEEE International Conference on Orlando, FL, USA Jun. 27-Jul. 2, 1994, New York, NY, USA IEEE, (Jun. 27, 1994), Seiten 3326-3331, XP0101277708 ISBN:0-7803-1901-X Seite 3328, Absatz 2—Seite 3330, letzter Absatz; Abbildungen 2-4.

* cited by examiner

METHOD FOR ESTABLISHING STRESS/STRAIN CURVES BY MEANS OF SPLINE INTERPOLATION ON THE BASIS OF CHARACTERISTIC POINTS AND WITH THE USE OF NEURAL NETWORKS

The invention relates to a method for establishing a stress/strain curve, as well as to a corresponding computer program product and a neural network.

It is known from the prior art that, in order to determine the mechanical properties of a material, tensile tests are carried out in which stress/strain curves are measured. Establishing the loading limits by means of stress/strain curves is significant, in particular, for plastics. Stress/strain curves form an important basis for the design of plastic parts.

The procedure of the tensile tests for plastics is defined in International Standard ISO 527, or in European Standard DIN EN 20527. In such a tensile test, a sample body is investigated with respect to its tensile deformation behaviour, its strength, its tensile modulus and other characteristics of the tensile stress/strain relationship. Multipurpose sample bodies according to DIN EN 23167 are preferably used for a tensile test.

Important parameters for the tensile tests are the measurement length and the testing rate. The typical mechanical characteristics are the yield stress, the failure stress, the tensile strength, the stress at a specific strain, the yield strain, the failure strain, the strain at the tensile strength, the nominal failure strain, the nominal strain at the tensile strength and the tensile modulus.

During a tensile test, a complete stress/strain curve is recorded, in which the stress is represented as a function of the sample-body strains which occur. In stress/strain curves of tensile tests on plastics, for example, distinction can be made between three typical curve types.

FIG. 1 shows respective examples of such a type-classed curve profile. Curve a is found with viscous or brittle materials that have no yield point, its profile being relatively flat in the case of viscous materials, whereas it rises steeply in the case of brittle materials. Curve b occurs with viscous materials that have a yield point. The tensile strength and the failure stress are in this case greater than the yield stress. Curve c likewise occurs with viscous materials that have a yield point. The tensile strength lies at the yield point and is greater than the failure stress.

The disadvantages with determining mechanical material properties by measuring stress/strain curves is that a large number of different tensile tests with different parameter selection are needed in order to establish such stress/strain curves, which makes this very intensive in terms of time and cost. Because of the large number of parameters which need to be varied in practice, stress/strain tensile tests can cover only a small fraction of the possible variations.

It is therefore an object of the invention to provide an improved method for establishing a stress/strain curve, as well as a corresponding neural network and a computer program product.

The object of the invention is achieved, respectively, by the features of the independent patent claims. Preferred embodiments are indicated in the dependent claims.

The invention makes it possible to train one or more neural networks with a relatively small number of stress/strain tensile tests. The neural networks are then used to establish arbitrary stress/strain curves while varying the parameters, without further tensile tests actually having to be carried out.

A neural network is essentially characterized by three elements:

1. The computing operation in a neuron, in which the scaled input values are converted into the output signal with weighting factors. A scalar product of the weighted input values is formed within each processing unit. A so-called activation function is applied to this result value, and the corresponding value is delivered.

2. The neural network architecture, that is to say the way in which the neurons or neuron layers are logically interconnected.

3. The learning method, in which the arbitrarily selected weighting factors are adapted in such a way that the correct response is obtained. The learning method is carried out in a series of iteration steps, in which the discrepancies between the calculated and specified property values are minimized. The neural network thereby obtains knowledge of all functional dependencies in the learning set.

Neural networks usually consist of two or more layers of neurons, which are generally simulated by corresponding computer programs or are represented in hardware form by special computer chips. They are distinguished in that an input signal, which consists of different activity of the neurons in the first level, influences the activity of the neurons in the second level.

The nature of the influence is not initially set precisely, but rather is formed gradually in the course of the learning processes. For example, DE 198 41 820 A1 discloses a neural network based on fractal mapping functions.

According to a preferred embodiment of the invention, a number of characteristic points are first established from the measured stress/strain curve profiles when setting up the neural network. The characteristic points are then subjected to a transformation, preferably a factor analysis or a principal component transformation. The neural network is then trained by means of the characteristic points transformed in this way. The neural network trained using the transformed points has a more stable behaviour than a network trained with non-transformed points.

According to a further preferred embodiment, a separate neural network is trained for each stress/strain curve type. Furthermore, a neural network for determining the type of a stress/strain curve is trained based on input parameters; optionally, a principal component transformation of the type probabilities may also be employed here. This neural network then makes it possible to select one of the separate neural networks in accordance with the respective current type.

The invention will be described in more detail below with the aid of a preferred exemplary embodiment.

Figure 2:
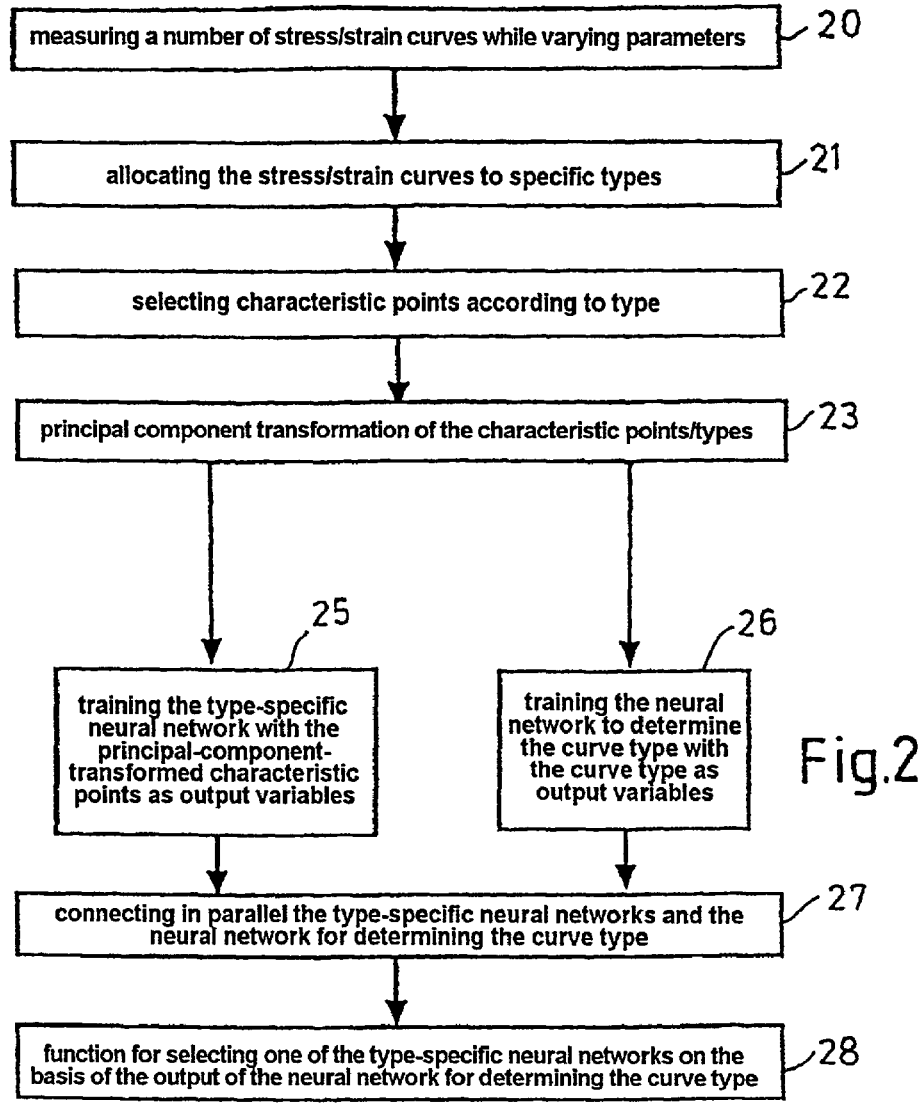
Figure 3:
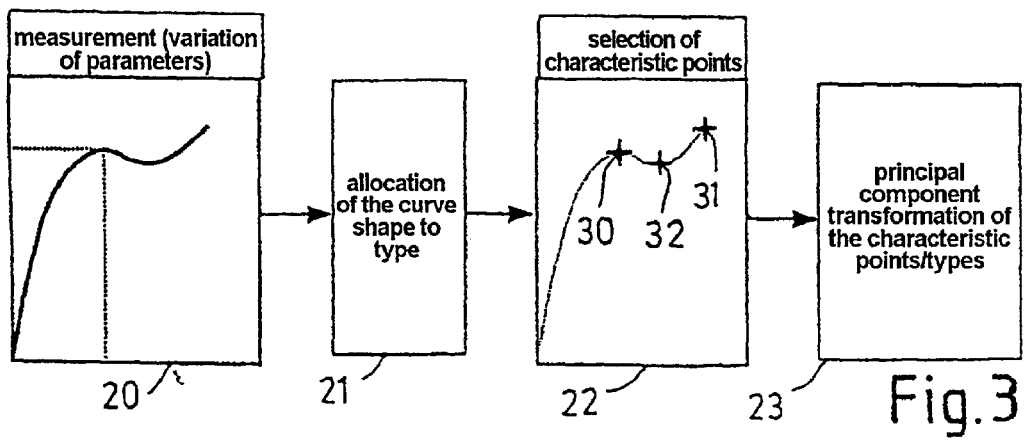
Figure 4:
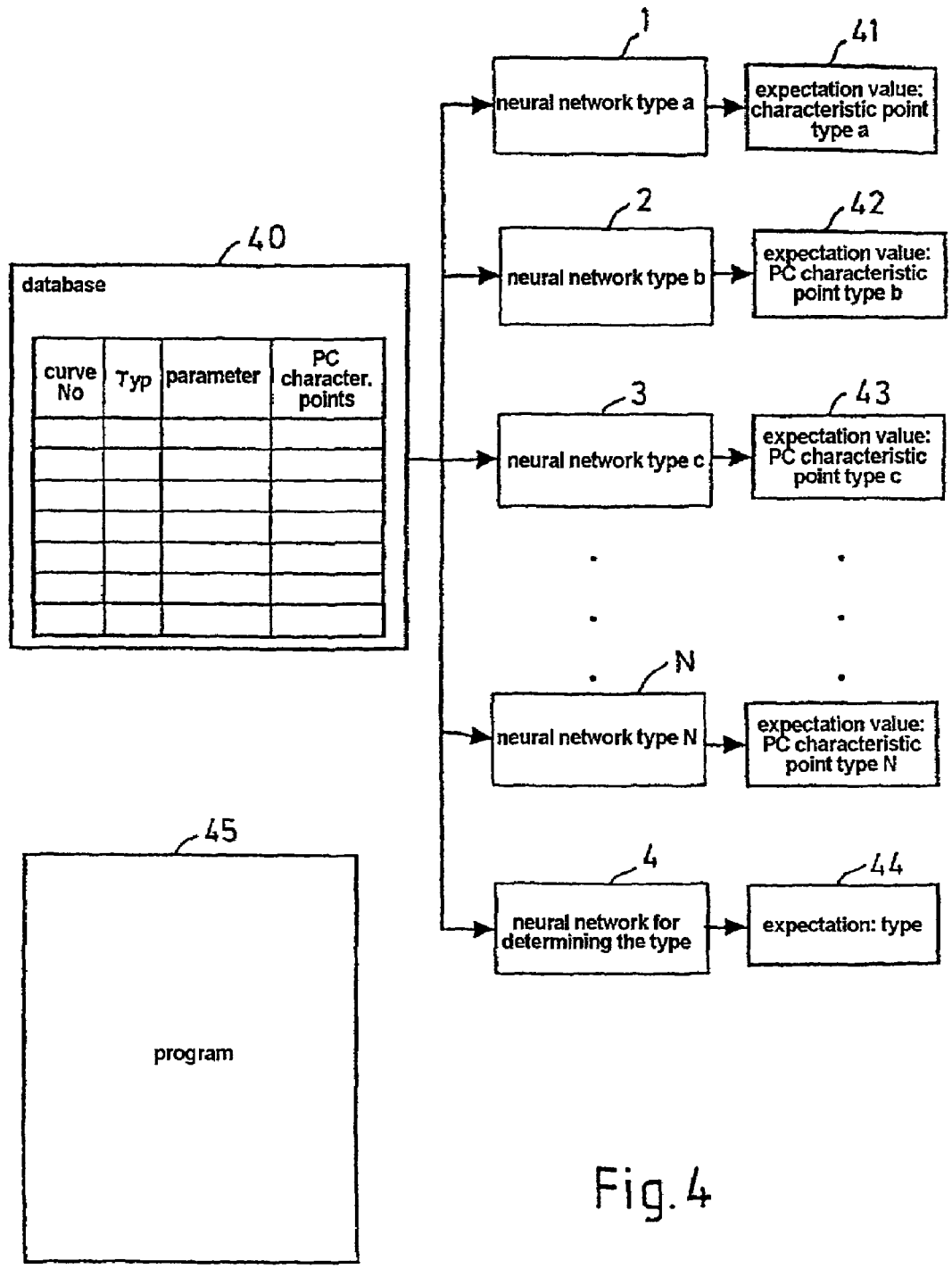
Figure 5:
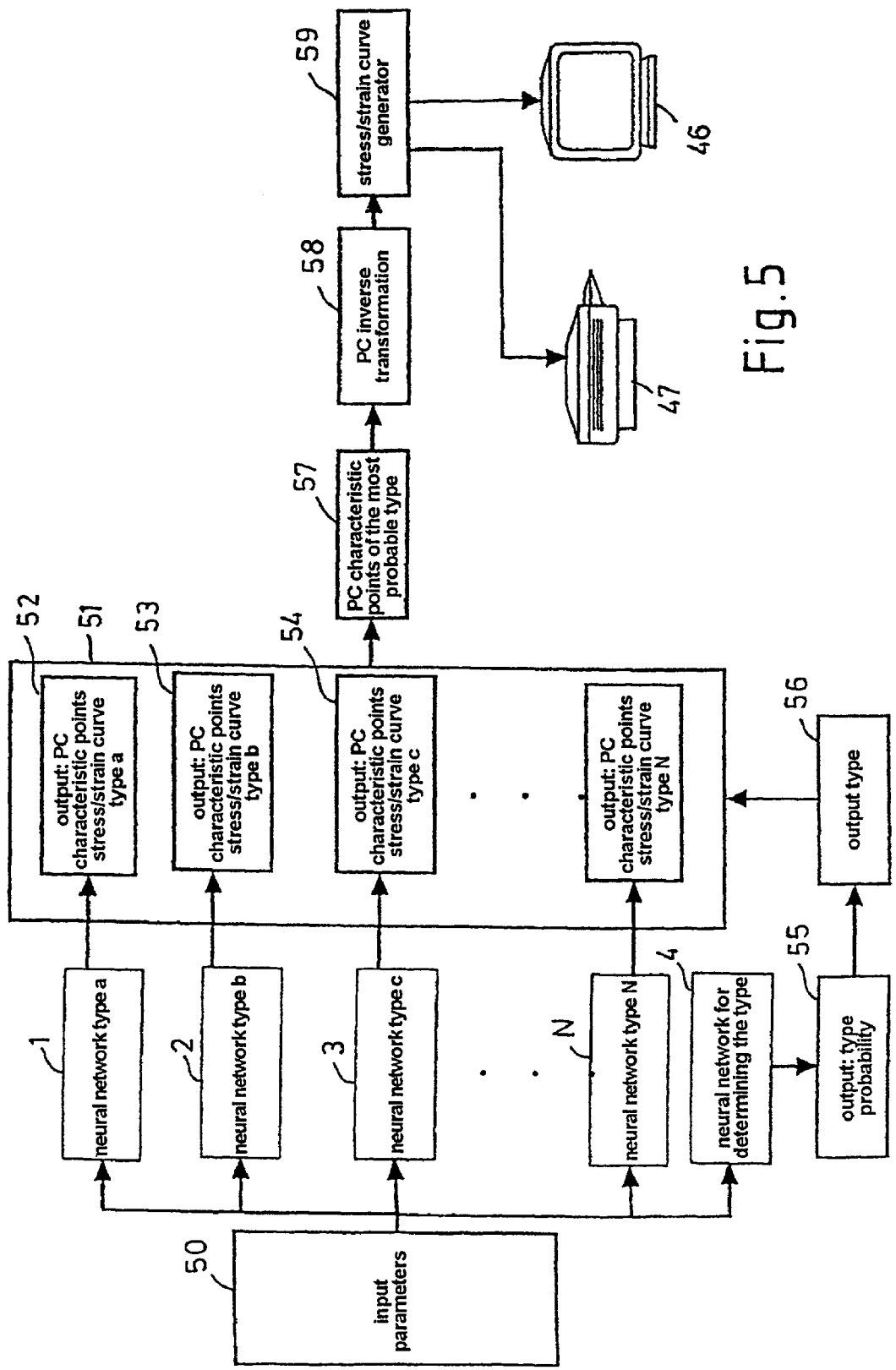
Figure 6:
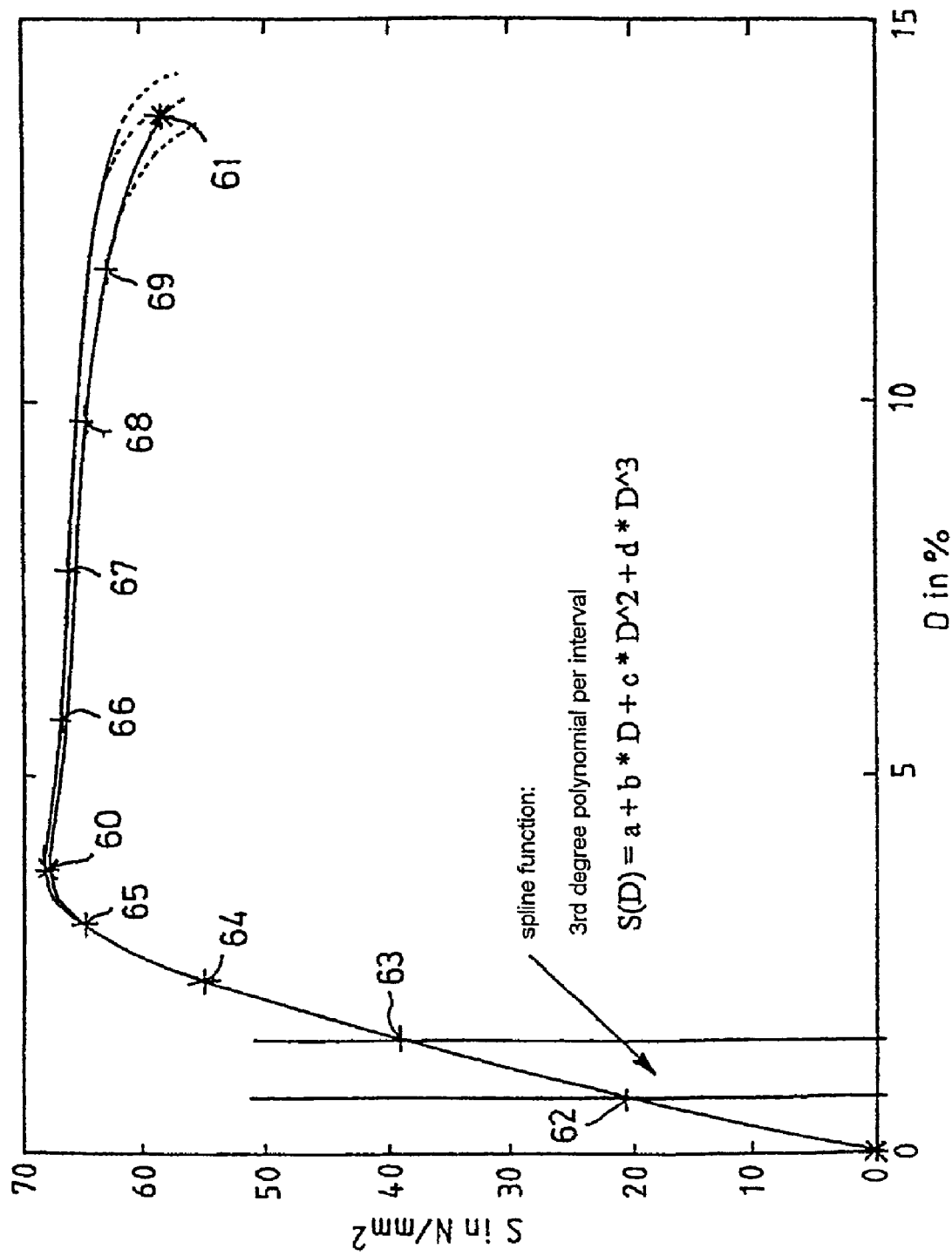
Figure 7:
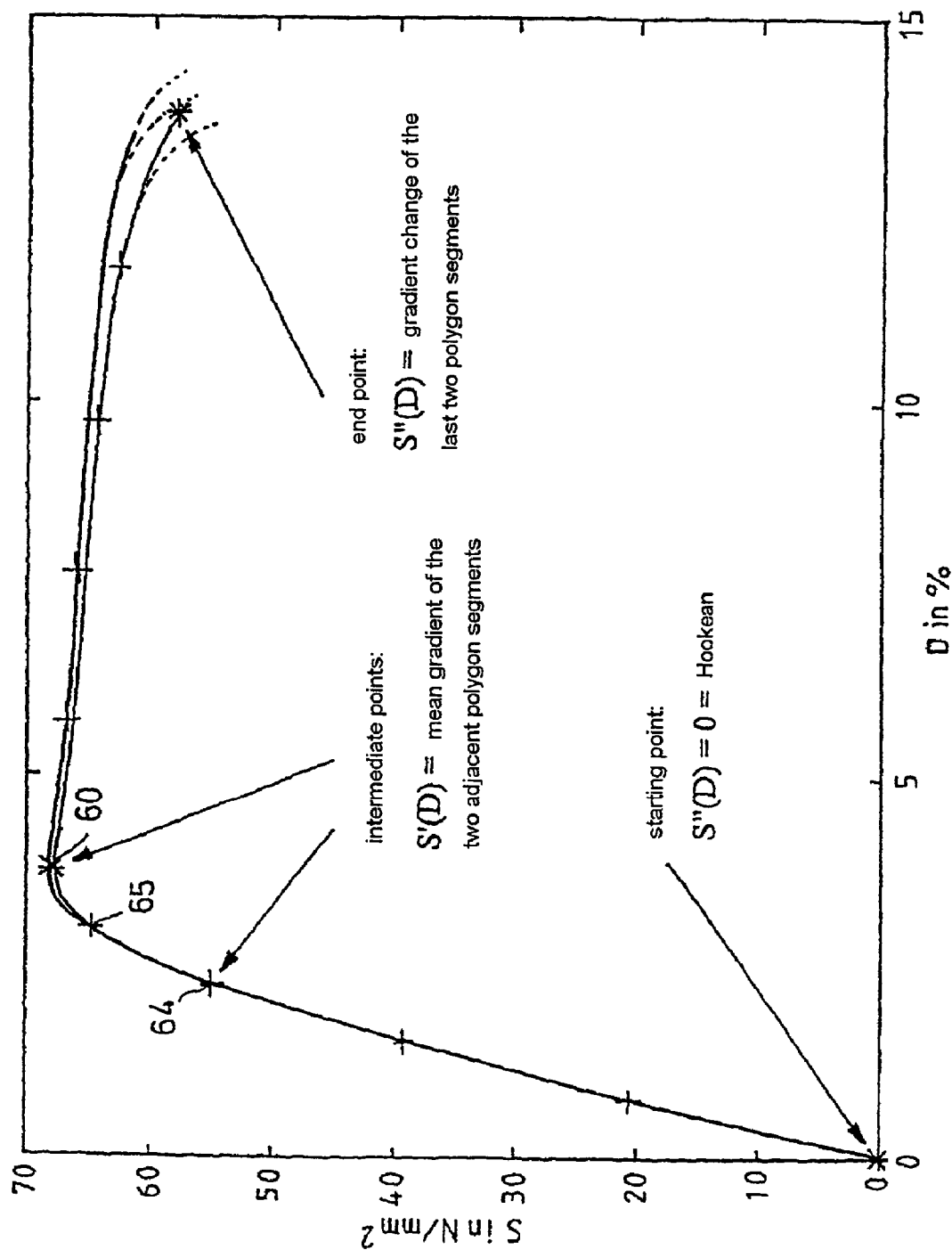
Figure 8:
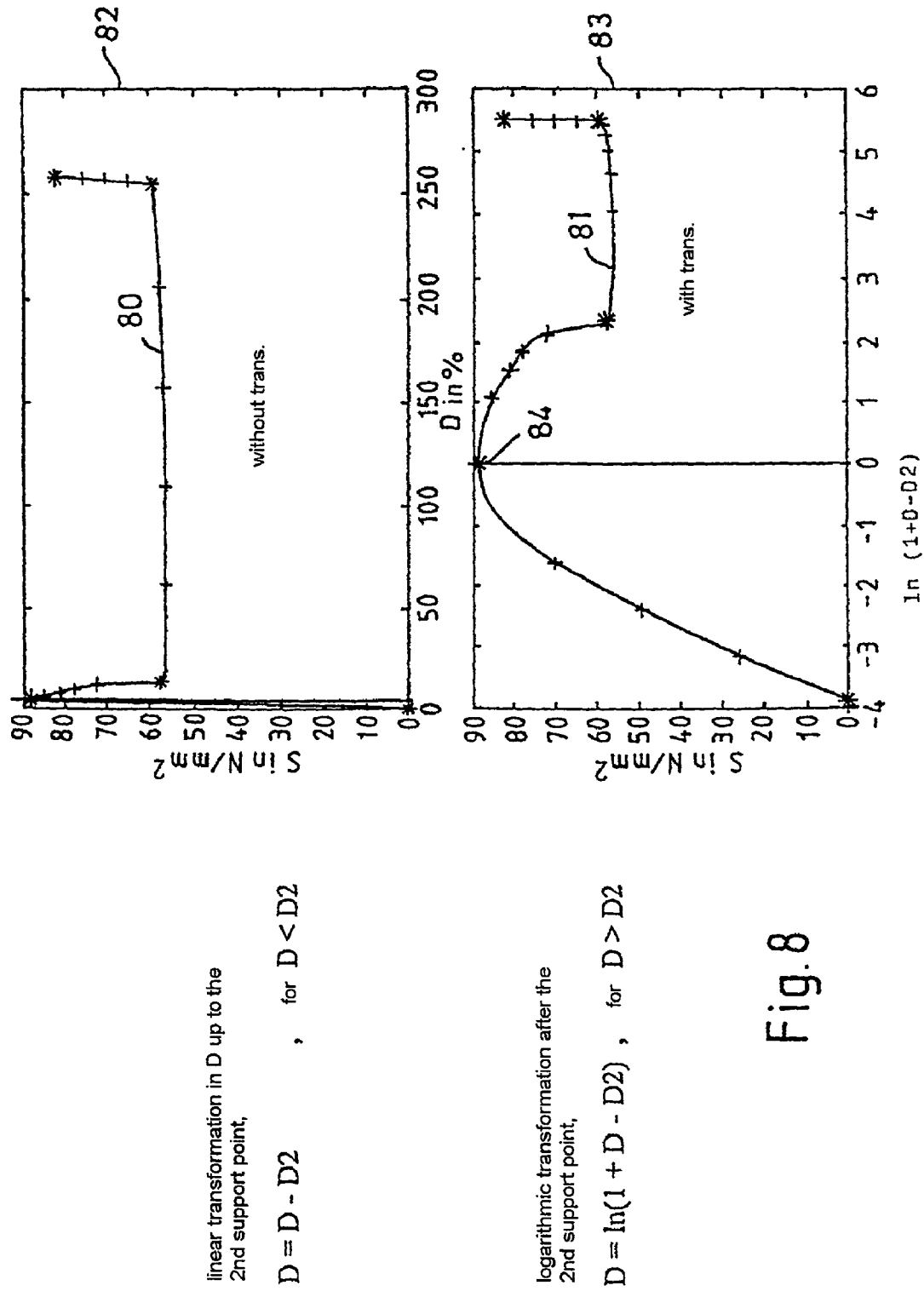

FIG. 1 shows a type-classification of stress/strain curves known from the prior art, FIG. 2 shows a flow chart of an embodiment of the method according to the invention for setting up a neural network, FIG. 3 shows a representation of the step sequence for establishing the principal components of the characteristic points from a stress/strain curve, FIG. 4 shows a block diagram for training the neural networks, FIG. 5 shows a block diagram of a neural network for determining a stress/strain curve on the basis of input parameters, FIG. 6 shows a representation of the selection of the characteristic points from a stress/strain curve, FIG. 7 shows a representation of the boundary conditions for the generation of stress/strain curves from characteristic points, FIG. 8 shows a representation of the stabilization of the spline interpolation by means of logarithmic scaling over a subinterval.

FIG. 2 shows a flow chart for generating a neural network to establish stress/strain curves. In step 20, tensile tests are firstly carried out to establish stress/strain curves while varying different parameters. The formulation, that is to say the material composition, as well as the colour and the component geometry can be varied, for example.

The processing conditions during the production of the sample body can furthermore be varied. In the case of an injection-moulded plastic part, these are for instance the compound temperature, the tool temperature and the final pressure. The conditions under which the tensile test is carried out can furthermore be varied, for instance the temperature to which the sample body is exposed while carrying out the tensile test.

The stress/strain curves established in such a measurement series are respectively allocated to a specific type in step 21. In this case, for example, the type classification according to FIG. 1 can be employed.

In step 22, a number of characteristic points are respectively selected for the type-classed stress/strain curves. The number of characteristic points, and their position, can vary depending on the type. For example, in the case of a stress/strain curve of curve type a (cf. FIG. 1), a single characteristic point, or a few characteristic points, may be sufficient since the curve essentially extends through the linear region.

In the case of a type-b stress/strain curve, at least three characteristic points are needed for recording the curve profile, namely the yield point, the failure point and the stress/strain curve minimum lying between the yield point and the failure point. Corresponding characteristic points can also be defined for a type-c curve and for other curve types.

In step 23, the characteristic points of the stress/strain curves are subjected to a principal component transformation. The principal component transformation reduces both noise and redundancy by carrying out a projection onto a relevant subspace in a multidimensional coordinate space. Principal component transformation is a mathematical method which is known per se.

A corresponding principal component transformation can also be carried out with respect to the curve type.

Before the respective principal component transformation is carried out, the transformation rule must firstly be established. This is done by arranging the previously established characteristic points of curves that have the same curve type in a matrix, and determining the parameters of the principal component transformation in order to bring the matrix into its principal component form. A corresponding procedure can also be adopted with respect to the transformation rule for the principal component transformation pertaining to the curve type.

In step 25, the parameters varied in step 20 are input into different neural networks connected in parallel. Each of the neural networks connected in parallel is in this case allocated to a specific curve type.

If the parameters have been input for a tensile test in which a stress/strain curve of a specific type was determined, then the output of the neural network corresponding to this curve type will be evaluated. The values output by the neural network of the relevant type are compared with the principal-component-transformed characteristic points which were established in step 23 for the tensile test in question. On the basis of a difference between the values output by the neural network and the values actually established by the principal component transformation in step 23, feedback into the neural network is provided in order to adapt the weighting of the neurons according to the value difference.

By sequentially inputting the various parameters and by respectively matching the calculated values with the values obtained by measurement and principal component transformation, the various types of neural networks are then trained stepwise.

Furthermore, a neural network for determining the curve type from the parameters is also trained in step 26. To that end, the corresponding parameters are input into a neural network whose output is intended to show the probabilities for the existence of a specific curve type. The output of this neural network is respectively matched by means of the actually existing curve type, or with the principal component transformation of the actually existing curve type, and the weighting of the neurons is adapted accordingly. This neural network for determining the curve type is also trained stepwise by applying the various parameters and subsequently matching with the actual curve type.

The type-specific neural networks, with the principal-component-transformed characteristic points as output variables, are trained for all stress/strain curves of the measurement series carried out in step 20. Steps 25 and 26 can take place in parallel, since the input vector, that is to say a specific set of parameters per stress/strain curve, can be the same in each case for the different neural networks.

In step 27, the type-specific neural networks as well as the neural network for determining the curve type, which were respectively established in steps 25 and 26, are connected in parallel. In step 28, a function is generated for selecting one of the type-specific neural networks.

The function receives the output of the neural network for determining the curve type, that is to say the respective probabilities for the existence of a specific curve type. The function establishes the maximum from among the various type probabilities and selects the particular neural network which corresponds to the most probable curve type. Therefore, when the overall neural network configured in this way is being operated, the curve type can firstly be determined on the basis of the input parameters in order to select the corresponding type-specific neural network.

FIG. 3 illustrates the way in which the principal-component-transformed characteristic points are established from a measured stress/strain curve. The steps in FIG. 3, which correspond to the steps in FIG. 2, have in this case been denoted by the same reference numbers. In step 20, a stress/strain curve is firstly measured in the presence of specific parameters, that is to say with a specific material composition, colour of the material, geometry of the sample body, processing parameters during the plastic injection-moulding as well as a specific temperature, testing rate and/or further parameters when carrying out the tensile test. Such measurements are carried out repeatedly for different variations of the parameters, that is to say with different material compositions, colours, component geometries, etc.

In step 21, the measured curve shape is allocated to a specific type. In step 22, characteristic points are then selected depending on the curve type. In the example in FIG. 3, the stress/strain curve involves a type-b curve (cf. FIG. 1), so that at least the yield point 30, the failure point 31 and the point 32 lying between the yield point 30 and the failure point 31 are accordingly selected. Further measurement points between these points can be selected automatically, for example at equidistant strain increments, as characteristic points.

In step 23, the characteristic points obtained in this way from all measured stress/strain curves of the same type are subjected to a principal component transformation, in order firstly to establish the parameters for carrying out the principal component transformation. The calculation rule established in this way is then used for the principal component transformation of the characteristic values of the individual curves. The principal-component-transformed types can also be correspondingly established for the neural network for determining the type probability.

FIG. 4 shows a block diagram of a computer system for training the neural networks. The computer has a database 40 which contains a data record for each measured stress/strain curve. The data record for a stress/strain curve contains the type of the curve (for example type a, b or c—cf. FIG. 1) and/or the corresponding principal components as well as the principal components (PCs) of the transformed characteristic points. The data record furthermore contains the parameters that are varied for each curve.

It is particularly advantageous for only the characteristic points, rather than all the measured values established when recording a stress/strain curve, to be stored in the database. This permits, for example, a data reduction from approximately 60,000 measurement values to fewer than 30 characteristic points.

The database is connected to the neural networks 1 to N. The database 40 is furthermore connected to the neural network 4 for determining the curve type. Each of the neural networks 1 to N and 4 has a corresponding output 41 to 43 and 44, respectively.

The computer system furthermore has a program 45 for reading specific data from the data records stored in the database and for training the neural networks 1 to N and 4.

In order to train the neural networks, the program 45 firstly reads the parameters of the data record of the first curve from the database 40. The parameters which have been read out are then applied to the inputs of the neural networks 1 to N and of the neural network 4.

The program 45 furthermore reads the curve type of the current curve from the database 40. According to the curve type, the output of the corresponding neural network is then read. If the first curve is, for example, of type c, then the output 43 will be read.

The values stored in the output 43 are compared with the actual principal components of the characteristic points. The weighting of the neural network for curve type c is adapted accordingly from the difference between the calculated and actual principal components of the characteristic points.

At the same time, the neural network 4 is trained by reading the expectation value, or its PCs, from the output 44. The probabilities, which are established by the neural network 4, for the existence of a specific curve type are compared with the actual curve type, or the corresponding PCs, as stored in the database 40 for the relevant curve—curve type c in the example in question. The neural network is here adapted accordingly from the discrepancy of the established probabilities with the curve type actually present.

FIG. 5 shows the resulting neural network for determining a stress/strain curve. The system has an input 50 for inputting the parameters. The input 50 is connected to the inputs of the neural networks 1 to N, as well as to the input of the neural network 4. The system furthermore has an output 51 with the memories 52, 53, 54 . . . respectively for the neural networks 1 to N. The memories 52, 53, 54 . . . are respectively connected to the output of the corresponding neural network 1, 2, 3 . . . .

The neural network 4 has an output 55 for outputting the type probabilities, or their PCs. In the program module 56, the curve type is selected on the basis of the type probability, optionally after a corresponding inverse transformation. The program module 56 selects a corresponding memory from among the memories 52, 53, 54 . . . contained in the output 51. The content of this memory is read from the corresponding memory by the program module 57 and subjected to an inverse transformation of the principal components in the program module 58.

On the basis of the inverse-transformed principal components, a stress/strain curve is then generated in the stress/strain curve generator 59. The stress/strain curve generated in this way can, for example, be displayed on a monitor 46 or printed out on a printer 47.

FIG. 6 shows the selection of characteristic points by a user. In the case of the curve type in FIG. 6, for example, the characteristic points 60 and 61 are selected by the user. The intermediate points 62 to 68 are then automatically set equidistantly and used automatically as further characteristic points.

The characteristic points 60 to 68 selected in this way are stored in the generator 59, and the generator 59 shows the result of the stress/strain curve calculation to the user in the same representation for checking. The user has the option to shift both the manually set characteristic points (any direction) and the automatically set intermediate points (vertically only), in order to optimize the curve established by the generator 59. For the curve calculated by the generator 59, a third degree spline polynomial is in this case used per interval, the respective characteristic points being used for the approximation.

FIG. 7 shows further boundary conditions for the generation of a stress/strain curve from the selected characteristic points. The start of the stress/strain curve calculated by the generator 59 lies at the origin. The second derivative of the calculated curve S is equal to 0 at the origin—which corresponds to the so-called Hookean region.

For all intermediate points 62 to 69 (in FIG. 6) which lie on the calculated curve, the mean gradient of the adjacent polygon segments is taken into account when establishing the spline polynomials. The calculation at the end point 61 (in FIG. 6) of the stress/strain curve, however, is based on the gradient change of the last two polynomial segments.

It is furthermore advantageous to parameterize the stress/strain curve as a curve with an artificial "time", in order to avoid overshoots. The generator 59 may furthermore contain a sorting function. In physical terms, the strain of the sample body can only become greater as the stress increases. For a calculated curve profile which reflects this physical situation, the curve profile can be corrected by sorting the strain values.

FIG. 8 shows the stress/strain curves 80 and 81. The stress/strain curve 80 has a very steep profile in its starting region. Since, however, the linear starting region is of particular relevance in practice, it is recommendable to extend it by a suitable transformation:

The stress/strain curve 81 is obtained from the stress/strain curve 80 by the use of logarithmic scaling for the strain D in the curve region after that characteristic point 84. The curvature behaviour of the transformed curve is thereby standardized and the spline interpolation method is stabilized.

| List of References | |
|---|---|
| neural network | 1 |
| neural network | 2 |
| neural network | 3 |
| neural network | 4 |
| neural network | N |
| output | 5 |
| yield point | 30 |
| failure point | 31 |
| point | 32 |
| database | 40 |
| output | 41 |
| output | 42 |
| output | 43 |
| output | 44 |
| program | 45 |
| monitor | 46 |
| printer | 47 |
| input | 50 |
| output | 51 |
| memory | 52 |
| memory | 53 |
| memory | 54 |
| output | 55 |
| program module | 56 |
| program module | 57 |
| program module | 58 |
| generator | 59 |
| characteristic point | 60 |
| characteristic point | 61 |
| intermediate point | 62 |
| intermediate point | 63 |
| intermediate point | 64 |
| intermediate point | 65 |
| intermediate point | 66 |
| intermediate point | 67 |
| intermediate point | 68 |
| intermediate point | 69 |
| stress/strain curve | 80 |
| stress/strain curve | 81 |
| diagram | 82 |
| diagram | 83 |
| characteristic point | 84 |

The invention claimed is:

1. Stress/strain curve generator for calculating a stress/strain curve by means of characteristic values and/or corresponding intermediate values, a piecewise approximation being carried out in subintervals to calculate the stress/strain curve, where the characteristic points are calculated by a neural network and principal component inverse transformation on a computer.

2. A method for setting up a neural network comprising:
 a) measuring a plurality of stress/strain curves that differ one from the others by at least one parameter,
 b) selecting a plurality of characteristic points for each of the stress/strain curves and
 c) training a neural network with said at least one parameter as input variable(s) and the corresponding characteristic points as output variables.

3. The method according to claim 2, wherein the at least one parameter relate to a member selected from the group consisting of formulation, color, component geometry, processing conditions and test conditions.

4. The method according to claim 2, wherein the selection is based on at least the following values of a stress/strain curve:
 a) the yield point,
 b) the failure point,
 c) one or more minima and/or points of the maximum curvature, residing between the yield point and the failure point on the stress/strain curve.

5. The method according to claim 2, wherein the selection is based on at least the following values of a stress/strain curve:
 a) the yield point,
 b) the failure point,
 c) one or more minima and/or points of the maximum curvature, residing between the yield point and the failure point an the stress/strain curve and
 d) one or more intermediate points, which are generated automatically.

6. The method according to claim 2, wherein each of the stress/strain curves is established several times without varying the at least one parameter.

7. The method according to claim 2, wherein the characteristic points are subjected to a transformation and the neural network is trained with the transformed characteristic points as output variables.

8. The method according to claim 7, wherein the transformation is a factor analysis or principal component transformation.

9. The method according to claim 2, wherein the stress/strain curves are type-classed and a separate neural network is trained for each type of a stress/strain curve.

10. The method according to claim 9, wherein a further neural network is trained with the parameter(s) as input variable(s) and the type or the principal components of the type of the stress/strain curve as output variables.

11. The method according to claim 10, wherein the separate neural networks and the further neural network are connected in parallel and the output of the separate neural network with the type having the highest probability is selected based on the output of the further neural network.

12. A method for establishing a stress/strain curve comprising:
 a) setting up a neural network using a method according to claim 2,
 b) inputting the parameter(s) into the neural network,
 c) outputting the characteristic points from the neural network,
 d) generating the stress/strain curve from the characteristic points.

13. The method according to claim 12, wherein the neural network having the type with the highest probability is selected.

14. The method according to claim 2, wherein the strains are sorted.

15. The method according to claim 14 wherein, the strain is logarithmically scaled in a later subinterval.

16. A neural network prepared by the method according to claim 2.

* * * * *